United States Patent
Doubler et al.

(10) Patent No.: US 11,141,199 B1
(45) Date of Patent: Oct. 12, 2021

(54) LARGE SHANK POLYAXIAL PEDICLE SCREW SYSTEM

(71) Applicant: Ortho Innovations, LLC, Palm Beach Gardens, FL (US)

(72) Inventors: Robert L. Doubler, Monroe, MI (US); John E. Hammill, Sr., Maumee, OH (US)

(73) Assignee: Ortho Innovations, LLC, Palm Beach Gardens, FL (US)

( * ) Notice: Subject to any disclaimer, the term of this patent is extended or adjusted under 35 U.S.C. 154(b) by 0 days.

(21) Appl. No.: 17/017,058

(22) Filed: Sep. 10, 2020

(51) Int. Cl.
*A61B 17/70* (2006.01)

(52) U.S. Cl.
CPC ........ *A61B 17/7032* (2013.01); *A61B 17/704* (2013.01)

(58) Field of Classification Search
None
See application file for complete search history.

(56) References Cited

U.S. PATENT DOCUMENTS

| | | | |
|---|---|---|---|
| 5,879,350 A * | 3/1999 | Sherman | A61B 17/7037 606/266 |
| 7,686,835 B2 | 3/2010 | Warnick | |
| 7,942,909 B2 | 5/2011 | Hammill, Sr. et al. | |
| 7,951,173 B2 * | 5/2011 | Hammill, Sr. | A61B 17/7034 606/269 |
| 9,549,765 B2 * | 1/2017 | Vedula | A61B 17/8625 |
| 2004/0236330 A1 | 11/2004 | Purcell et al. | |
| 2006/0293665 A1 | 12/2006 | Shluzas | |
| 2008/0004625 A1 * | 1/2008 | Runco | A61B 17/7037 606/273 |
| 2008/0009862 A1 | 1/2008 | Hoffman | |
| 2008/0015596 A1 * | 1/2008 | Whipple | A61B 17/8685 606/86 A |
| 2010/0125302 A1 * | 5/2010 | Hammill, Sr. | A61B 17/7038 606/308 |
| 2010/0312288 A1 * | 12/2010 | Hammill, Sr. | A61B 17/7037 606/305 |
| 2015/0201972 A1 * | 7/2015 | Doubler | A61B 17/7002 606/266 |

* cited by examiner

*Primary Examiner* — Tessa M Matthews
(74) *Attorney, Agent, or Firm* — McHale & Slavin, P.A.

(57) ABSTRACT

A pedicle screw fastening system that consists of an anchoring bone screw having a first diameter with threads on one end for use in anchoring the screw to the bone and a spherical ball connector member having a second diameter on the other end, with the second diameter smaller than the first diameter; the spherical ball connector member operating as a pivot point about which a connecting assembly moves in a polyaxial fashion. The connecting assembly has a lower connector member with an attachment ring to secure the spherical ball connector member, allowing the use of the small diameter spherical ball connector member with a large shank anchoring bone screw. A biased retainer member maintains a positive tension between the connecting assembly and the anchored screw. The system allows for large shank screws with small connecting assemblies.

5 Claims, 7 Drawing Sheets

LARGE SHANK POLYAXIAL PEDICLE SCREW SYSTEM

FIELD OF THE INVENTION

This invention is directed to the field of pedicle screws, and in particular, to a pedicle screw system having large shank anchors for use with small connector assemblies.

BACKGROUND OF THE INVENTION

The use of pedicle screw fasteners is well known for their use with spinal fixation systems. A conventional polyaxial bone screw typically consists of a shank with a bone thread at one end for threading into the bone. A spherical ball connector member is positioned at an opposite end for coupling to a connecting assembly. Surgically implanted fixation systems are commonly used to correct a variety of back structure problems, including those which occur as a result of trauma or improper development during growth. A commonly applied fixation system includes the use of one or more stabilizing rods aligned in a desired orientation with respect to a patient's spine using pedicle screws for the anchoring of the fixation system.

Common to all spinal implant systems is the necessity for proper anchoring to the bone to provide support for linking rods and connector assemblies. The use of a polyaxial pedicle screw has proven very effective in allowing a surgeon the flexibility to secure an installation with minimal strain on the individual. However, one problem with a polyaxial pedicle screw is the lack of a stabilized angular placement position during installation if the bone is soft or damaged. The prior art has limited options to use various size anchoring screws in combination with a common saddle, which leads to assembly integrity over a large range of installation considerations.

Applicant's U.S. Pat. No. 7,942,909 discloses a thread-thru polyaxial pedicle screw fastening system. The fastening system consists of an anchoring bone screw having threads on one end for use in anchoring the screw and a spherical ball connector member on the other end operating as a pivot point about which a U-shaped connecting assembly moves in a polyaxial fashion. The system allows for an improved manufacturing step wherein the threaded shank of a bone screw can be passed through a lower portion of the connecting assembly, allowing larger shanks to be placed through a connector assembly. The connector assembly would have to be sized sufficiently to allow the larger shank to pass through.

Applicant's U.S. Pat. No. 7,951,173 discloses a pedicle screw fastening system that consists of an anchoring bone screw having threads on one end for use in anchoring the screw and a spherical connector on the other end operating as a pivot point about which a U-shaped or side loading connecting assembly is used to secure to a connecting rod for use in stabilization of a spine. The connecting assembly, for receipt of a spinal connecting rod, includes a biased retainer ring for maintaining a positive tension between the connecting assembly and the anchored screw. The system allows for an improved manufacturing step wherein the threaded shank of a bone screw can be passed through a lower portion of the connecting assembly, allowing a variety of bone screw sizes to be used with a common sized connector.

There remains a need for larger shank anchoring screws for use with small connector assemblies.

SUMMARY OF THE INVENTION

The present invention is a polyaxial pedicle screw system that permits a large sized anchoring screw to be used with a small sized spherical ball connector member, allowing securement to a low profile connecting assembly. The connecting assembly is defined by an upper connector member having a first centrally located aperture with first and second sidewalls forming a U-shaped opening therebetween, and a lower connector member having a second centrally located aperture. During the manufacturing stage, the spherical ball connector member is placed through the lower connector member aperture, wherein an attachment ring is pressed over the spherical ball connector member and positioned along a lower surface thereof to prevent removal of the lower connector member from the spherical ball connector member. A spring biased saddle component is positioned on the upper surface of the spherical ball connector member and the upper connector member is then welded to the lower connector member.

The design permits the manufacturer to use a range of larger sized shanks while using a small spherical ball connector member so as to minimize the size of the connecting assembly. In many instances the height of the connection assembly is critical, whereby the use of a small spherical ball connector member allows a substantial reduction in the connector member height, as opposed to use of the same diameter spherical ball connector member to an associated shank, which is the common practice.

A biasing member allows a surgeon to move the connector assembly to a desired angular position; compression springs will keep tension on the spherical ball connector member to maintain the connector assembly in the angular position. This facilitates the installation of a rod, as the connector assembly can be rotated into a position for proper placement of the connecting rod, but the proper angle of the connection assembly can be maintained, allowing the surgeon to align additional screws for ease of rod placement. A fastener set screw is utilized to attach the connection of a rod to the upper connector, the rod pressing the saddle component into contact with the spherical ball connector member while simultaneously causing the lower surface of the spherical ball connector member to wedge against the attachment ring, which in turn wedges against the lower connector member, thereby immobilizing the connector assembly.

The connector members are rigid structures adapted to link an associated anchoring assembly with one of the stabilizing rods. The stabilizing rods may be rigid or dynamic members shaped to form a spine-curvature-correcting and/or immobilizing path. Attaching each anchoring assembly, via connectors, to a stabilizing rod forces a patient's back into a surgeon-chosen shape. Stabilizing rods may be used singly, or in pairs, depending upon the type of correction required. The rods vary in size, but typically extend between at least two vertebrae.

Accordingly, it is an objective of the invention to provide a spinal screw assembly capable of capturing a larger diameter shank than could otherwise be assembled through the inside diameter of a small sized connector assembly by incorporating an attachment ring to secure the shank to the connector assembly.

It is another objective of the invention to provide a small connector assembly, both in diameter and height, wherein a smaller spherical head is required on the anchoring member.

It is still another objective of the invention to use an attachment ring to reinforce a lower connector member, and provide a construction that prevents movement of the attachment ring upwardly or downwardly upon installation.

It is a further objective of the present invention to teach the use of a polyaxial pedicle screw system for posterior fixation having a common connector for use with different sized shanks and thread types, which lowers inventory requirements and provides the surgeon with a uniform connector.

It is another objective of the present invention to disclose the use of a polyaxial pedicle screw having a biasing member to supply a tension between the anchoring member and the connector member; the tension facilitates installation by maintaining the connector component in an angular placement position as desired by the surgeon.

It is another objective of the present invention to provide a factory assembled, large shank, polyaxial pedicle screw assembly that allows use of a common sized connector assembly to lower the cost of manufacture and lessen inventory.

Yet another objective of the present invention is to teach the use of a polyaxial bone screw assembly that allows about 60 degrees of conical polyaxial motion.

It is yet another objective of the present invention to provide a simple spinal fixation system having only a few components for use in assembly and limiting component parts needed during assembly, making the device simple to assemble.

Other objectives and advantages of this invention will become apparent from the following description taken in conjunction with the accompanying drawings wherein are set forth, by way of illustration and example, certain embodiments of this invention. The drawings constitute a part of this specification, include exemplary embodiments of the present invention, and illustrate various objects and features thereof.

DETAILED DESCRIPTION OF THE PREFERRED EMBODIMENT

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Referring generally to the Figures, disclosed is an exemplary embodiment of the polyaxial pedicle screw system for use in a spinal fixation system (10) based on an anchoring member (12) having a shank (14) of a first diameter d1 with at least one helical thread (16) formed along the length thereof. At an upper end of the shank (14) is a neck (20) leading to a spherical ball connector member (18) having a second diameter d2, the second diameter d2 is less than the first diameter d1. The spherical ball connector member (18) and the diameter of the shank (14) controls the maximum angular positioning, which is about 60 degrees in relation to a connector assembly (30).

Figure 7:
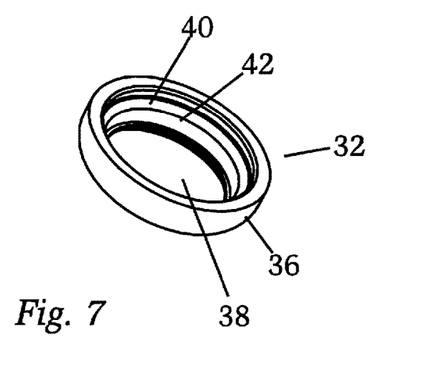
FIG. 7 is an upper perspective view of the lower connector member.
Figure 8:
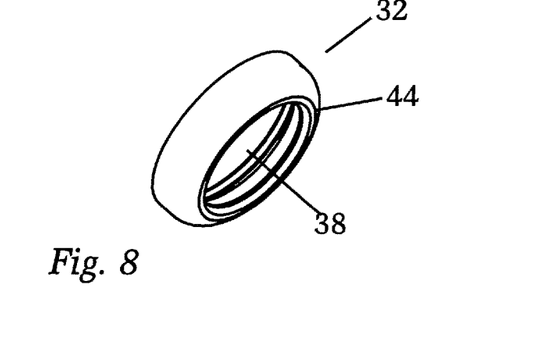
FIG. 8 is a lower perspective view of the lower connector member.
Figure 9:
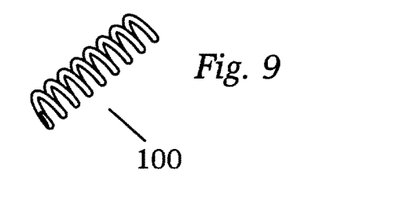
FIG. 9 is a side view of the compression spring.
Figure 10:
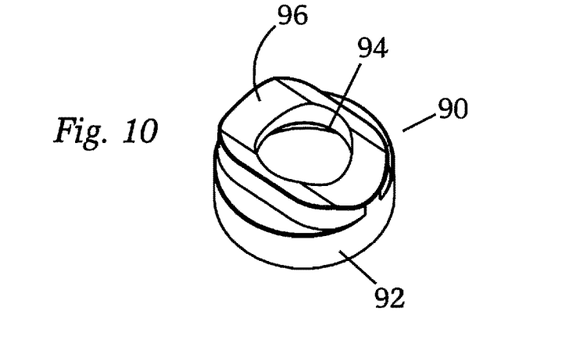
FIG. 10 is an upper perspective view of the saddle component.
Figure 11:
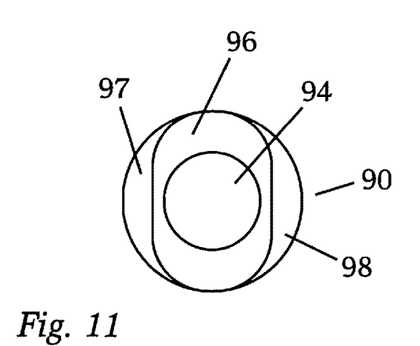
FIG. 11 is a top plane view of the saddle component.
Figure 12:
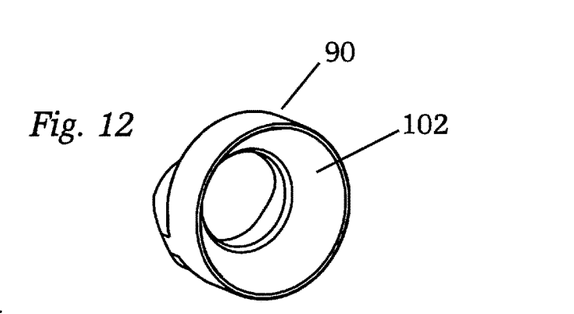
FIG. 12 is a lower perspective view of the saddle component.
Figure 13:
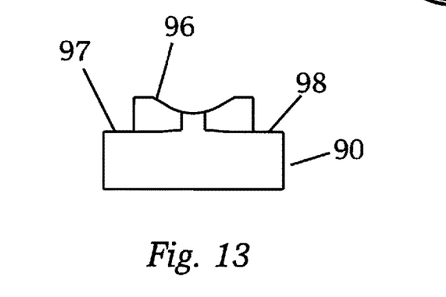
FIG. 13 is a side view of the saddle component.
Figure 14:
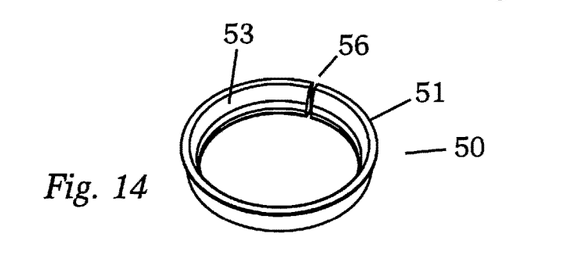
FIG. 14 is an upper perspective view of the attachment ring.
Figure 15:
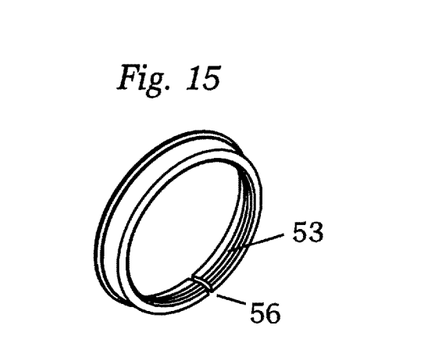
FIG. 15 is a lower perspective view of the attachment ring.
Figure 16:
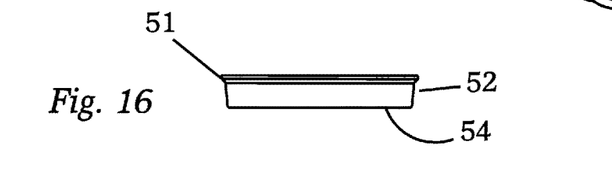
FIG. 16 is a side view of the attachment ring.

The connector assembly (30) is attached to the anchoring member (12) during a manufacturing stage. The connector assembly (30) is defined by a lower connector member (32) and an upper connector member (34). Referring to FIGS. 7-8, the lower connector member (32) has a circular side wall (36) with a centrally disposed aperture (38). An inner side wall (40) has a ledge (42) formed parallel to a bottom edge (44) for receipt of an attachment ring (50). Referring to FIGS. 14-16, the attachment ring (50) is formed from a side wall (51) having an outer surface (52) with a shape that is constructed and arranged to engage the inner side wall (40) of the lower connector member (32), and an inner side wall (53) constructed and arranged to receive a portion of the lower surface (19) of the spherical ball connector member (18). A bottom edge (54) is formed at about a right angle to the inner side wall (40) for engaging the ledge (42) of the lower connector member (32) when assembled. The attachment ring (50) has a break (56) in the sidewall (51) of a predetermined size that allows the attachment ring (50) to be placed over the spherical ball connector member (18) during assembly.

Figure 17:
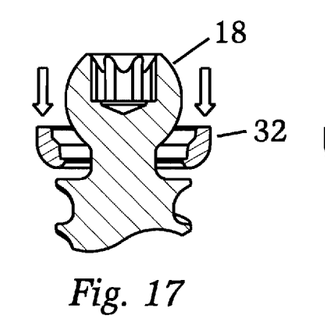
FIG. 17 is a cross sectional view depicting placement of the spherical ball connector member through the lower connector member.
Figures 18, 19:
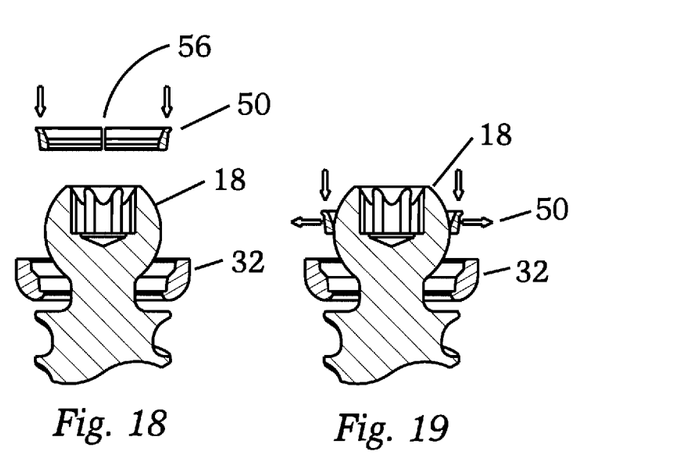
FIG. 18 is a cross sectional view depicting assembly of the attachment ring to the spherical ball connector member.
FIG. 19 is a cross sectional view depicting assembly of the attachment ring over the spherical ball connector member.
Figures 20, 21:
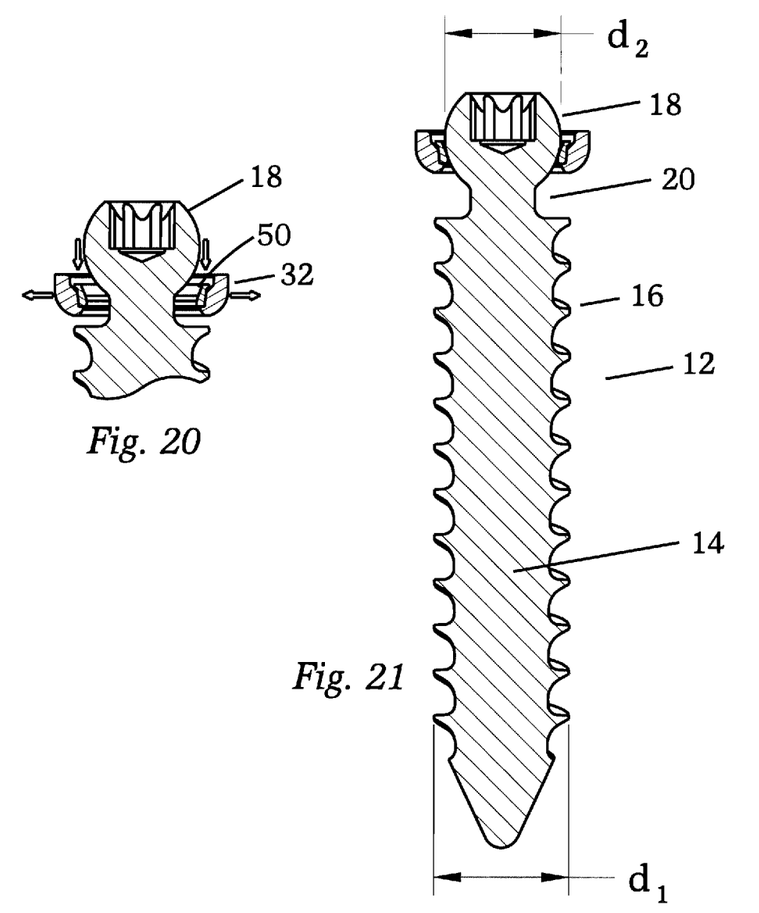
FIG. 20 is a cross sectional view depicting the positioning of the attachment ring in position relative to the lower connector member.
FIG. 21 is a cross sectional view depicting the assembly of the screw to the lower connector member with the attachment ring.
Figure 22:
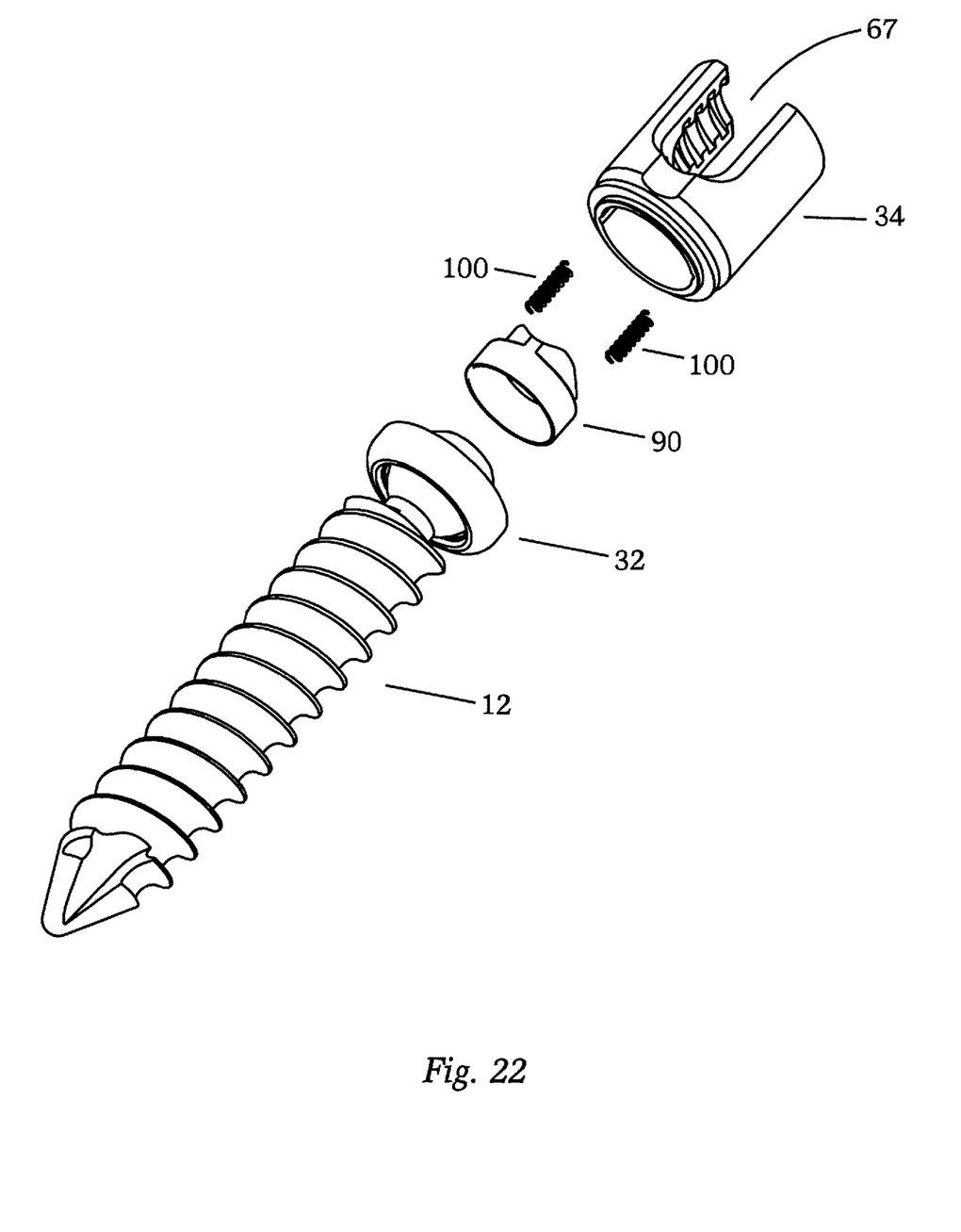
FIG. 22 is an exploded view of the pedicle screw assembly.
Figures 23, 24, 25:
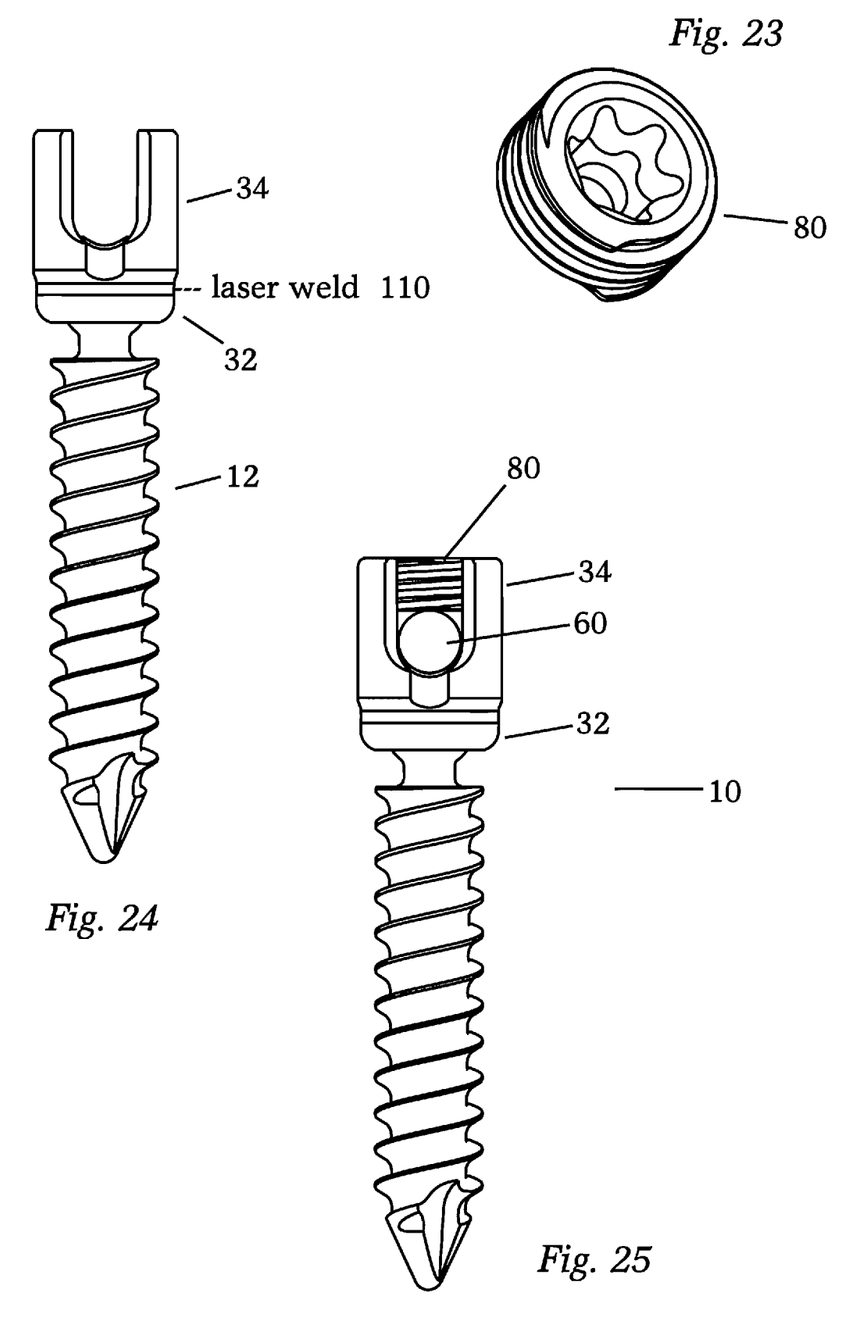
FIG. 23 is a perspective view of the cap screw.
FIG. 24 is a side view depicting the welding location of the upper connector member to the lower connector member.
FIG. 25 is a side view depicting the assembly with a secured rod.

Referring to FIG. 17, illustrated is the lower connector member (32), which has a continuous inner side wall (40), placed over the spherical ball connector member (18) through the aperture (38). It is noted that the spherical ball connector member (18) passes through the aperture (38) without interference. FIG. 18 illustrates the attachment ring (50) with the break (56) positioned over the spherical ball connector member (18) in a position ready for placement. FIG. 19 illustrates the attachment ring (50) expanded as it is placed over the spherical ball connector member (18). FIG. 20 illustrates the attachment ring (50) interfacing with the lower connector member (32).

Figures 1, 2:
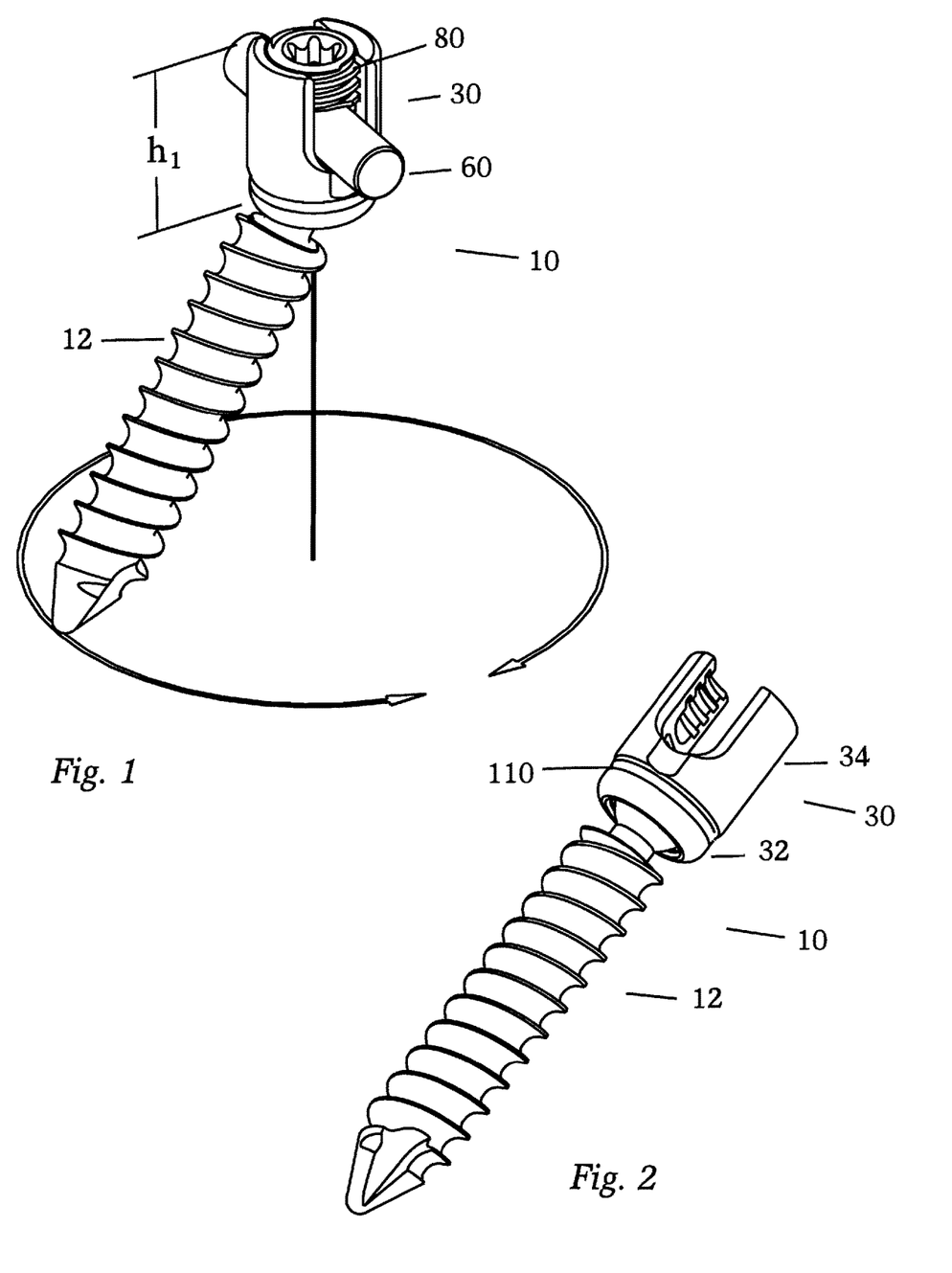
FIG. 1 is a perspective view of a screw assembly shown locked with a rod and tilted to a maximum axial angle.
FIG. 2 is a perspective view of the screw assembly, depicting a large diameter shank.
Figure 4:
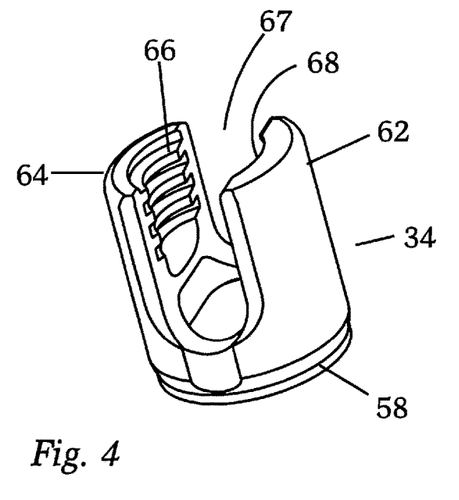
FIG. 4 is an upper perspective view of an upper connector member.
Figure 5:
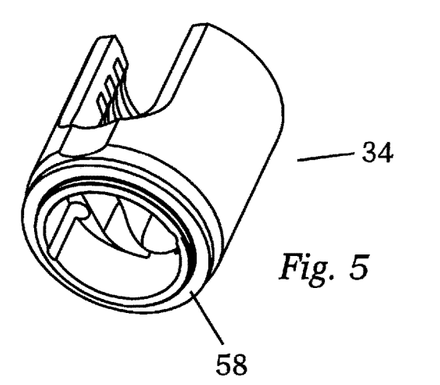
FIG. 5 is a lower perspective view of the upper connector member.
Figure 6:
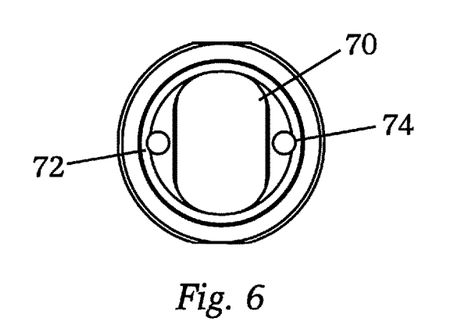
FIG. 6 is a bottom view of the upper connector member.

Referring to FIGS. 4-6, the upper connector member (34) is formed of a continuous side wall (58) having a first and second upstanding side wall (62, 64) forming a U-shaped opening (67) therebetween sized for receipt of a connecting rod (60) shown in FIG. 1. Side walls (62) and (64) include internal threads (66) and (68) for receipt of a fastener (80) commonly referred to as a set screw. The upper connector member (34) has an oblong shaped aperture (70) with first and second compression spring sockets (72, 74) positioned on each side of the oblong shaped aperture (70) for receipt of a compression spring (100). It should be noted that while the compression springs (100) are illustrated as coil springs, any spring or resilient type member suitable for displacing the saddle component may be utilized without departing from the scope of the invention. Such springs or resilient members may include, but should not be limited to, Belleville type springs, leaf springs, polymeric members and suitable combinations thereof.

Referring to FIGS. 10-13, illustrated is a saddle (90) having a cylindrical sidewall (92) with a centrally located aperture (94). An upper surface (96) is concave shaped for receipt of a connection rod (60), shown in FIG. 1, with support ledges (97 and 98) positioned on each side of the concave shaped upper surface (96). A lower surface (102) of the saddle (90) is spherical shaped and coincides with the shape of the spherical ball connector member 18. The upper surface (96) of the saddle (90) provides additional surface area for contact with the connecting rod, and may include a knurled or otherwise modified surface finish adapted to enhance gripping power between the rod (60) and the upper connector member 34. The saddle (90) is constructed and arranged to cooperate and frictionally engage the spherical ball connector member (18) to prevent rotation when fully assembled.

Figure 3:
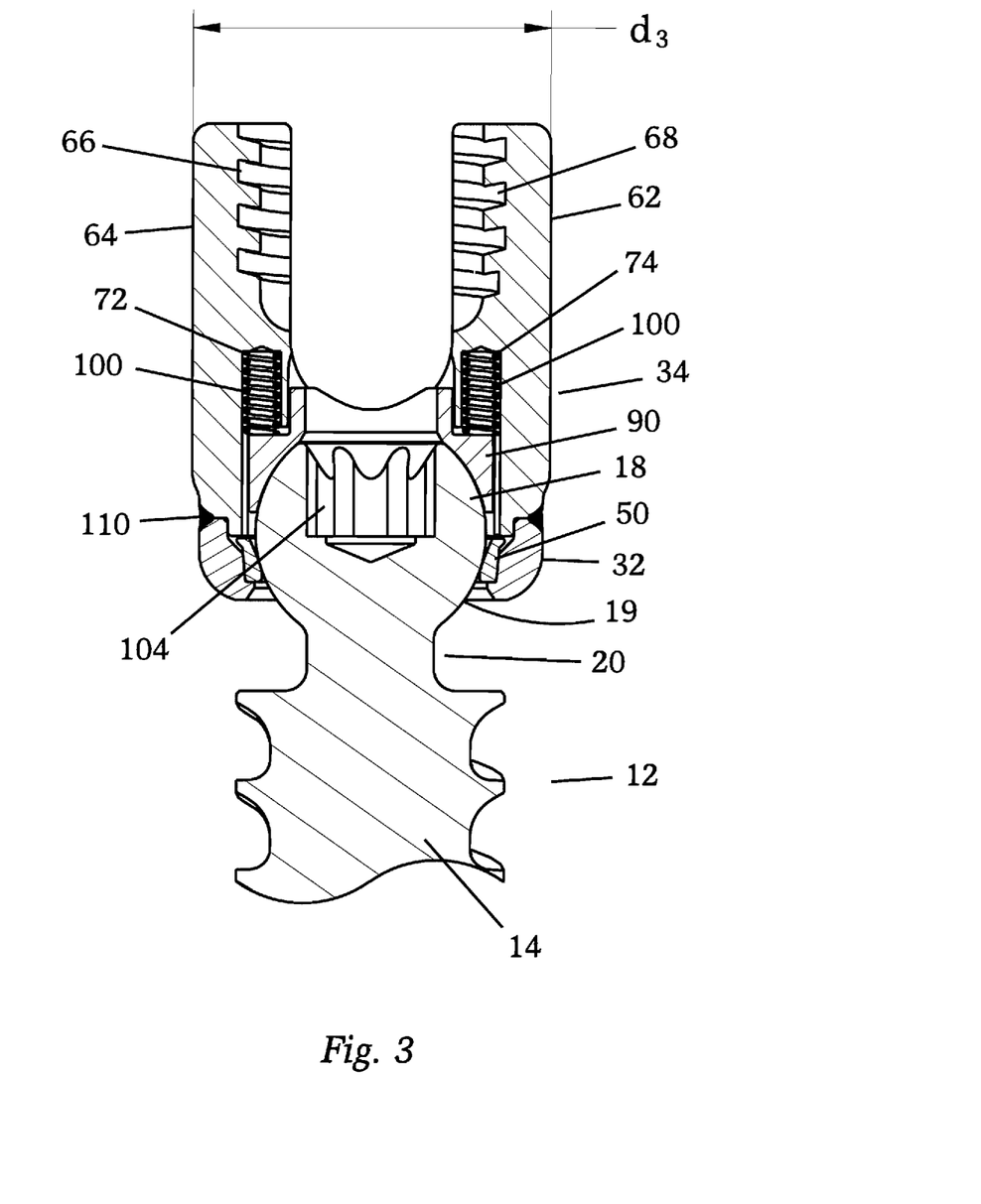
FIG. 3 is a cross section side view.

As illustrated in FIGS. 1-3, the lower connector member (32) is connected to the upper connector member (34) by a weldment (110) wherein compression springs (100) fit within spring sockets (72, 74) for biasing the saddle 90 against the spherical ball connector member (18). The biasing provides sufficient pressure on the spherical ball connector member (18) to maintain the upper connector member (34) in a set position to assist in installation. The anchoring member (12) is threaded into bone structure by use of a driving receptacle (104). It should be noted that the driving receptacle (104) may be any shape, male or female, suitable for cooperation with a driving tool, not shown, to rotate the anchoring member (12) into its final position. It is also important to note that the proportions of the anchoring member (104) depicted are for illustrative purposes only and variations in the length of the shank, diameter of the screw, thread pitch, thread length, number of thread leads, shank induced compression and the like may be varied without departing from the scope of the invention. Unique to the present invention is the ability to use various oversized shank diameters having a spherical ball connector member of a smaller diameter, thereby allowing for the use of connector assemblies that are small in diameter d3 and in height h1. The lower connector member (32) is constructed and arranged to provide a wedge shaped configuration upon receipt of the attachment ring (50) used to engage the spherical ball connector member (18). The tighter the pull on the shank (14), the more secure the spherical ball connector member (18) will be lodged against the attachment ring (50), which in turn is lodged against the inner surface (40) of the lower connector member (32), making it impossible to separate.

The saddle (90) cooperates with inner side wall (40) of the aperture 38 to prevent rotation of the saddle component. The lower surface (102) of the saddle component has a spherical diameter and provides for self centering by engaging of the outer surface of the spherical ball connector member (18). The saddle component (90) operates with the biasing member springs 100 to cause a tension between the saddle (90) and the spherical ball connector member (18). In the preferred embodiment, the biasing member is coil springs (100) that are located to cooperate with spring pockets (72, 74) positioned in the upper connector member (34) to locate and contain the springs (100). Once the anchoring member (12) is secured to the bone, a rod (60) placed within the upper connector member (34) fits within the U-shaped opening (67). The fastener (80) is threaded onto the threads (66, 68) of the connector member (34), wherein the rod (60) forces the saddle (90) onto the spherical ball connector member (18), locking the assembly into a fixed position. Alternatively, the upper connector member (34) can include the use of the well know faster type wherein the upper connector side wall has external threads and the fastener element would be a nut having internal threads.

The method of constructing a pedicle screw system through the steps comprising: forming a lower connector member having a second centrally disposed aperture; selecting a one piece anchoring member having a large threaded shank of a first diameter and a spherical ball connector member of a second diameter, said second diameter being less than said first diameter; inserting said spherical ball connector member into said lower connector member second aperture; placing an attachment ring over said spherical ball connector member and positioning said attachment ring between a lower surface of said spherical ball connector member and an upper surface of said lower connector member; forming an upper connector member having a bottom wall with a first centrally disposed aperture and two upstanding side walls forming a U-shaped opening traverse to said aperture for receipt of a rod, said side walls being threaded for receipt of a fastener to secure the rod thereto; positioning a saddle between a lower surface of said upper connector member and an upper surface of said spherical ball connector member; attaching a biasing member between said upper connector member and said saddle; and welding said upper connector member to said lower connector member; wherein said pedicle system is used for situations whereby a large threaded shank and a small connector assembly is desired.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The invention claimed is:

1. A pedicle screw system comprising:
    an anchoring member having a one piece threaded shank and a spherical ball connector member;
    a connecting assembly defined by a lower connector member having an aperture sized for receipt of said spherical ball connector member and an upper connector member having a U-shaped opening for receipt of a connecting rod member;
    a saddle biased against said upper connector member and engaging an upper surface of said spherical ball connector member;
    an attachment ring positioned stationary between said lower connector member and said upper connector member, said attachment ring having an inner surface interfacing with a bottom surface of said spherical ball connector member, and a split side wall outer surface constructed and arranged to engage an inner side wall of said lower connector member and said upper connector member to prevent upward movement of said attachment ring, said attachment ring preventing removal of said spherical ball connector member from said lower connector member; and
    a fastener element securable to said upper connector and shaped for engaging a rod member between an upper surface of said saddle and said U-shaped opening;
    wherein said shank has a first diameter and said spherical ball connector member has a second diameter, said second diameter being less than said first diameter, whereby said attachment ring is positioned along the bottom surface of said spherical ball connector before said lower connector member is welded to said upper connector member, said upper connector preventing upward movement of said attachment ring.

2. The pedicle screw system according to claim 1 wherein the saddle is biased with a biasing member, said biasing member is defined as a compression spring having a first end positionable in a spring pocket of said upper connector member and a second end cooperating with an upper surface of said saddle.

3. The pedicle screw system according to claim 1 wherein said saddle includes a cylindrically concave upper surface for cooperation with said rod.

4. The pedicle screw system according to claim 1 wherein said saddle extends into said U-shaped opening.

5. The pedicle screw system according to claim 1 wherein said upper connector member includes an internal thread and said fastener element is further defined as a set screw.

* * * * *